US00PP20023P2

(12) United States Plant Patent
Perkins

(10) Patent No.: US PP20,023 P2
(45) Date of Patent: May 26, 2009

(54) ***COREOPSIS* PLANT NAMED 'CORE YEL'**

(50) Latin Name: *Coreopsis hybrida*
Varietal Denomination: Core Yel

(75) Inventor: Ralph T. Perkins, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/150,464

(22) Filed: Apr. 28, 2008

(51) Int. Cl.
*A01H 5/00* (2006.01)

(52) U.S. Cl. ..... Plt./417

(58) Field of Classification Search ..... Plt./417
See application file for complete search history.

*Primary Examiner*—Annette H Para
(74) *Attorney, Agent, or Firm*—C. A. Whealy

(57) ABSTRACT

A new and distinct cultivar of *Coreopsis* plant named 'Core Yel', characterized by its compact, upright and somewhat outwardly spreading plant habit; vigorous growth habit; freely branching habit; freely flowering habit; flat and full single inflorescences with bright yellow-colored ray florets and a red-colored "eye"; and strong peduncles.

2 Drawing Sheets

Botanical designation: *Coreopsis hybrida.*
Cultivar denomination: 'Core Yel'.

BACKGROUND OF THE INVENTION

The present invention relates to a new and distinct cultivar of *Coreopsis* plant, botanically known as *Coreopsis hybrida,* and hereinafter referred to by the name 'Core Yel'.

The new *Coreopsis* originated from an open-pollination during the summer of 2002 in Gilroy, Calif. of an unnamed proprietary selection of *Coreopsis grandiflora*×*Coreopsis lanceolata,* not patented, as the female, or seed, parent with an unknown selection of *Coreopsis hybrida,* as the male, or pollen, parent. Seeds resulting from the open pollination were sown in March, 2003. The new *Coreopsis* was discovered and selected by the Inventor as a single flowering plant from within the progeny of the stated open-pollination in a controlled greenhouse environment in Gilroy, Calif. in September, 2003.

Asexual reproduction of the new *Coreopsis* by vegetative cuttings in a controlled greenhouse environment in Gilroy, Calif. since September, 2003, has shown that the unique features of this new *Coreopsis* are stable and reproduced true to type in successive generations.

SUMMARY OF THE INVENTION

The cultivar Core Yel has not been observed under all possible environmental conditions. The phenotype may vary somewhat with variations in environment such as temperature and light intensity, without, however, any variance in genotype.

The following traits have been repeatedly observed and are determined to be the unique characteristics of 'Core Yel'. These characteristics in combination distinguish 'Core Yel' as a new and distinct cultivar of *Coreopsis:*

1. Compact, upright and somewhat outwardly spreading plant habit.
2. Vigorous growth habit.
3. Freely branching habit.

4. Freely flowering habit.
5. Flat and full single inflorescences with bright yellow-colored ray florets and a red-colored "eye".
6. Strong peduncles.

Plants of the new *Coreopsis* differ from plants of the female parent selection in the following characteristics:

1. Plants of the new *Coreopsis* are more compact than plants of the female parent selection.
2. Plants of the new *Coreopsis* are more freely branching than plants of the female parent selection.
3. Plants of the new *Coreopsis* have larger inflorescences than plants of the female parent selection.
4. Inflorescences of plants of the new *Coreopsis* have a larger and darker red-colored "eye" than plants of the female parent selection.

Plants of the new *Coreopsis* can be compared to plants of the *Coreopsis* 'Flying Saucer', not patented. In side-by-side comparisons conducted in Gilroy, Calif., plants of the new *Coreopsis* differed from plants of 'Flying Saucer' in the following characteristics:

1. Plants of the new *Coreopsis* were more compact than plants of 'Flying Saucer'.
2. Plants of the new *Coreopsis* had larger and flatter inflorescences than plants of 'Flying Saucer'.
3. Plants of the new *Coreopsis* and 'Flying Saucer' differed in inflorescence color as ray florets of plants of 'Flying Saucer' did not have a red-colored "eye".

BRIEF DESCRIPTION OF THE PHOTOGRAPHS

The accompanying photographs illustrate the overall appearance of the new *Coreopsis.* These photographs shows the colors as true as it is reasonably possible to obtain in colored reproductions of this type. Colors in the photographs may differ slightly from the color values cited in the detailed botanical description which accurately describe the colors of the new *Coreopsis.*

The first photograph comprises a side perspective view of a typical flowering plant of 'Core Yel' grown in a container.

The second photograph is a close-up view of typical inflorescences of 'Core Yel'.

Plants used in the aforementioned photographs were grown in Gilroy, Calif. during the summer for three months in 10-cm containers in a greenhouse and under conditions and practices which approximate those generally used in commercial *Coreopsis* production. During the production of the plants, day temperatures ranged from 24° C. to 32° C. and night temperatures averaged 18° C.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Gilroy, Calif. during the summer in ground beds in an outdoor nursery and under conditions and practices which approximate those generally used in commercial *Coreopsis* production. During the production of the plants, day temperatures ranged from 24° C. to 32° C. and night temperatures averaged 18° C. Measurements and numerical values represent averages for typical flowering plants. Plants were seven to nine months old when the description was taken.

Botanical classification: *Coreopsis hybrida* cultivar Core Yel.

Parentage:

*Female parent.*—Unnamed proprietary selection of *Coreopsis grandiflora*×*Coreopsis lanceolata,* not patented.

*Male parent.*—Unnamed selection of *Coreopsis hybrida,* not patented.

Propagation:

*Type.*—By vegetative cuttings.

*Time to initiate and develop roots.*—About three to four weeks at 20° C. to 23° C.

*Root description.*—Fibrous; white in color.

*Rooting, habit.*—Freely branching.

Plant description:

*Plant form/growth habit.*—Compact, upright and somewhat outwardly spreading plant habit; broad inverted triangle; freely branching habit with about four to six lateral branches; inflorescences held above and beyond the foliage on strong peduncles. Vigorous growth habit.

*Plant height.*—About 18 cm to 24 cm.

*Plant diameter or spread.*—About 16 cm to 20 cm.

*Lateral branches.*—Length: About 20 cm to 28 cm. Diameter: About 3 mm to 4 mm. Internode length: About 3 cm to 6 cm. Aspect: Mostly upright to outwardly spreading. Strength: Strong. Texture: Smooth, glabrous. Color: Close to 146B.

Foliage description:

*Arrangement.*—Opposite, simple; sessile.

*Length.*—About 10.5 cm to 10.8 cm.

*Width.*—About 1.5 cm to 2.3 cm.

*Shape.*—Narrowly elliptical.

*Apex.*—Rounded to slightly acute.

*Base.*—Attenuate.

*Margin.*—Entire.

*Texture, upper and lower surfaces.*—Smooth, glabrous.

*Venation pattern.*—Pinnate.

*Color.*—Developing and fully expanded foliage, upper surface: Close to 138A; venation, close to 138A. Developing and fully expanded foliage, lower surface: Close to 138A; venation, close to 138A.

Inflorescence description:

*Appearance.*—Flat and full single terminal and axillary inflorescences with ray and disc florets developing acropetally on a receptacle. Inflorescences positioned above and beyond the foliage on strong peduncles. Inflorescences face upright. Freely flowering habit; about 100 inflorescences developing per plant during the flowering season. Inflorescences persistent.

*Fragrance.*—None detected.

*Time to flower.*—Under natural season conditions, plants flower continuously from the spring through to the autumn in California.

*Post-production longevity.*—Inflorescences maintain good substance for about 10 to 14 days on the plant.

*Inflorescence bud.*—Height: About 9 mm to 10 mm. Diameter: About 1 cm to 1.3 cm. Shape: Globular. Color: Close to 7A.

*Inflorescence size.*—Diameter: About 5.5 cm to 6 cm. Disc diameter: About 1.4 cm to 1.5 cm. Receptacle height: About 1 mm to 1.5 mm.

*Ray florets.*—Shape: Narrowly spatulate. Length: About 2.7 cm to 2.6 cm. Width: About 1.7 cm to 1.8 cm. Apex: Emarginate; ragged appearance. Base: Truncate. Margin: Entire. Texture, upper and lower surfaces: Papillose. Number of ray florets per inflorescence: About eight arranged in a single whorl. Aspect: Flat. Color: When opening, upper and lower surfaces: Close to 17B. Fully developed, upper surface: Mid-section and towards the apex, close to 17B; towards the base, close to 183A, forming the "eye". Fully developed, lower surface: Mid-section and towards the apex, close to 12A; towards the base, underlain with close to 183A.

*Disc florets.*—Shape: Tubular; apex dentate. Length: About 7 mm. Diameter: About 1 mm. Number of disc florets per inflorescence: About 150 to 175. Color: Apex and mid-section: Close to 17A to 17B. Base: Close to 2C.

*Phyllaries.*—Quantity per inflorescence: About eight in a single whorl. Length: About 9 mm to 1.5 cm. Width: About 4 mm to 5 mm. Shape: Oblanceolate. Apex: Acute. Base: Truncate. Margin: Entire. Texture, upper and lower surfaces: Smooth, glabrous. Color, upper and lower surfaces: Towards the apex, close to 151A; towards the base, close to 144A.

*Peduncles.*—Length: About 13 cm to 22 cm. Diameter: About 2 mm. Strength: Strong. Aspect: Mostly upright to about 45° from vertical. Texture: Smooth, glabrous. Color: Close to 146B.

*Reproductive organs.*—Androecium: Quantity per disc floret: Five. Anther shape: Linear. Anther length: About 7 mm. Anther color: Close to 15A. Pollen amount: Moderate to abundant. Pollen color: Close to 23A. Gynoecium: Quantity per ray or disc floret: One. Pistil length: About 9 mm to 10 mm. Style length: About 6 mm to 7 mm. Style color: Close to 12C. Stigma length: About 1 mm. Stigma color: Close to 12B.

*Seed/fruit.*—Seed and fruit production has not been observed.

Disease/pest resistance: Plants of the new *Coreopsis* have not been shown to be resistant to pathogens and pests common to *Coreopsis*.

Garden performance: Plants of the new *Coreopsis* have exhibited good tolerance to rain and wind and have been observed to tolerate temperatures from about 4° C. to about 35° C.

It is claimed:

1. A new and distinct *Coreopsis* plant named 'Core Yel' as illustrated and described.

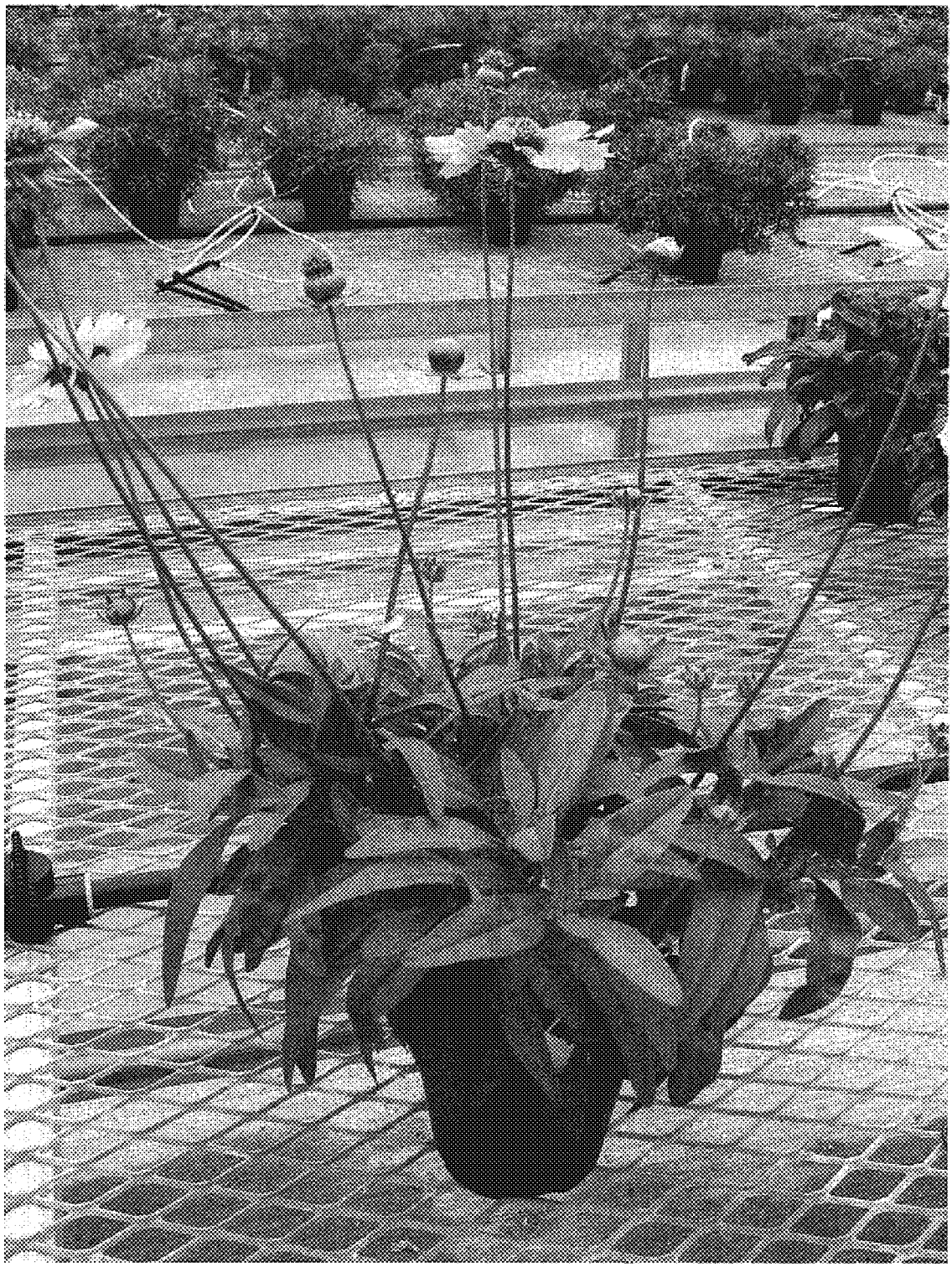

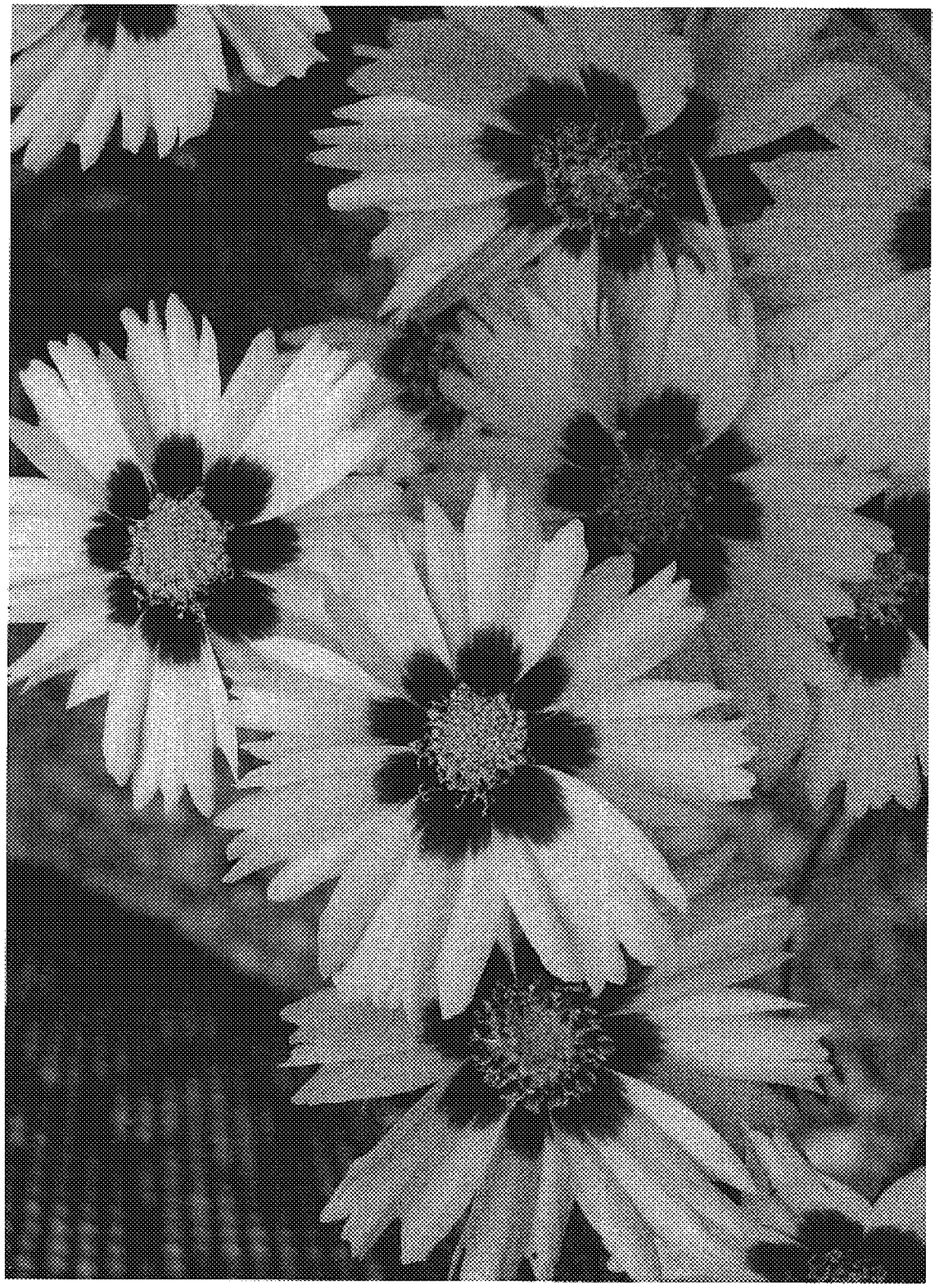

* * * * *